United States Patent
Kim et al.

(10) Patent No.: US 11,564,622 B2
(45) Date of Patent: Jan. 31, 2023

(54) APPARATUS AND METHOD FOR GENERATING METABOLISM MODEL

(71) Applicant: SAMSUNG ELECTRONICS CO., LTD., Suwon-si (KR)

(72) Inventors: Sang Kyu Kim, Yongin-si (KR); So Young Lee, Daejeon (KR); Ka Ram Choi, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 447 days.

(21) Appl. No.: 16/786,651

(22) Filed: Feb. 10, 2020

(65) Prior Publication Data
US 2020/0367815 A1    Nov. 26, 2020

(30) Foreign Application Priority Data
May 21, 2019    (KR) .................. 10-2019-0059349

(51) Int. Cl.
| | | |
|---|---|---|
| A61B 5/00 | (2006.01) | |
| G16H 10/60 | (2018.01) | |
| G06N 20/00 | (2019.01) | |
| A61B 5/145 | (2006.01) | |

(52) U.S. Cl.
CPC ........ *A61B 5/4866* (2013.01); *A61B 5/14532* (2013.01); *A61B 5/14546* (2013.01); *G06N 20/00* (2019.01); *G16H 10/60* (2018.01)

(58) Field of Classification Search
CPC .............. A61B 5/4866; A61B 5/14532; A61B 5/14546; G16H 10/60; G06N 20/00
USPC .......................................................... 702/19
See application file for complete search history.

(56) References Cited

U.S. PATENT DOCUMENTS

| | | | | |
|---|---|---|---|---|
| 2006/0167348 | A1* | 7/2006 | Arnold .................. | G01N 21/35 356/300 |
| 2011/0047108 | A1* | 2/2011 | Chakrabarty .......... | G16H 10/65 706/14 |
| 2012/0123234 | A1* | 5/2012 | Atlas .................... | A61B 5/7264 600/365 |
| 2013/0085772 | A1* | 4/2013 | Gaweda ................. | G16Z 99/00 705/2 |
| 2014/0297246 | A1* | 10/2014 | Albisser ................ | G16H 15/00 703/11 |
| 2014/0316759 | A1 | 10/2014 | Albisser et al. | |
| 2018/0064378 | A1 | 3/2018 | Park et al. | |
| 2018/0146854 | A1* | 5/2018 | Bergstrom ............ | G16H 40/67 |
| 2018/0240543 | A1 | 8/2018 | Maeda et al. | |
| 2019/0053742 | A1* | 2/2019 | Steil .................. | A61M 5/14244 |
| 2019/0110751 | A1 | 4/2019 | Lee et al. | |

FOREIGN PATENT DOCUMENTS

| | | |
|---|---|---|
| JP | 2012-088947 A | 5/2012 |
| KR | 10-2018-0027006 A | 3/2018 |
| KR | 10-2019-0043034 A | 4/2019 |
| WO | 2018/118714 A1 | 6/2018 |

\* cited by examiner

*Primary Examiner* — Kerri L McNally
(74) *Attorney, Agent, or Firm* — Sughrue Mion, PLLC

(57) ABSTRACT

An apparatus for generating a metabolism model may include a processor configured to obtain a predetermined number of bio-information profiles from a bio-sensor, extract a representative bio-information profile from the obtained predetermined number of bio-information profiles, and generate the metabolism model for correcting an error of the bio-sensor by using the extracted representative bio-information profile.

18 Claims, 6 Drawing Sheets

APPARATUS AND METHOD FOR GENERATING METABOLISM MODEL

CROSS-REFERENCE TO RELATED APPLICATION(S)

This application is based on and claims priority under 35 U.S.C. § 119 to Korean Patent Application No. 10-2019-0059349, filed on May 21, 2019, in the Korean Intellectual Property Office, the disclosure of which is incorporated by reference herein in its entirety.

BACKGROUND

1. Field

The disclosure relates to technology for bio-information measurement.

2. Description of Related Art

Diabetes is a chronic disease that causes various complications and can be difficult to cure, such that people with diabetes are advised to check their blood glucose regularly to prevent complications. In particular, when insulin is administered to control blood glucose levels, the blood glucose levels have to be closely monitored to avoid hypoglycemia and control insulin dosage.

Furthermore, glycemic response varies between individuals, despite having the same food intake, depending on their characteristics (e.g., age, sex, weight, region, race, etc.). Accordingly, there is a need to consider each individual's characteristics to improve accuracy in blood glucose measurement.

SUMMARY

Provided are an apparatus and method for generating a metabolism model for correcting errors of a bio-sensor.

Additional aspects will be set forth in part in the description which follows and, in part, will be apparent from the description, or may be learned by practice of the presented embodiments.

According to an aspect of the disclosure, an apparatus for generating a metabolism model may include a processor configured to obtain a predetermined number of bio-information profiles from a bio-sensor, extract a representative bio-information profile from the obtained predetermined number of bio-information profiles, and generate the metabolism model for correcting an error of the bio-sensor by using the extracted representative bio-information profile.

The bio-information profiles my correspond to a user's bio-information data measured by the bio-sensor during a predetermined period of time after food intake.

The predetermined number may be set based on an accuracy of the bio-sensor.

The predetermined number may be set to a greater value as the accuracy of the bio-sensor decreases.

The bio-information may be a concentration of an in vivo analyte, and the analyte may include at least one of glucose, triglyceride, urea, uric acid, lactate, protein, cholesterol, antioxidant, and ethanol.

The processor may extract the representative bio-information profile from the obtained predetermined number of bio-information profiles by using at least one of a mean value, a median value, filtering, and machine learning.

The processor may generate guide information for inducing a user to obtain the predetermined number of bio-information profiles, and provide the guide information to the user.

According to an aspect of the disclosure, a method of generating a metabolism model may include obtaining a predetermined number of bio-information profiles from a bio-sensor sensor, extracting a representative bio-information profile from the obtained predetermined number of bio-information profiles, and generating the metabolism model for correcting an error of the bio-sensor by using the extracted representative bio-information profile.

The bio-information profiles may correspond to a user's bio-information data measured by the bio-sensor during a predetermined period of time after food intake.

The predetermined number may be set based on an accuracy of the bio-sensor.

The predetermined number may be set to a greater value as the accuracy of the bio-sensor decreases.

The bio-information may be a concentration of an in vivo analyte, and the analyte may include at least one of glucose, triglyceride, urea, uric acid, lactate, protein, cholesterol, antioxidant, and ethanol.

The extracting of the representative bio-information profile may include extracting the representative bio-information profile from the obtained predetermined number of bio-information profiles by using at least one of a mean value, a median value, filtering, and machine learning.

The method may include generating guide information for inducing a user to obtain the predetermined number of bio-information profiles, and providing the guide information to the user.

A method of generating a metabolism model may include recognizing a user's food intake, based on recognizing the user's food intake, obtaining a predetermined number of bio-information profiles by using a bio-sensor, based on obtaining the predetermined number of bio-information profiles, extracting a representative bio-information profile from the obtained predetermined number of bio-information profiles, and generating the metabolism model for correcting an error of the bio-sensor by using the extracted representative bio-information profile.

The method may include repeating the recognizing of the food intake and the obtaining of the bio-information profiles until the predetermined number of bio-information profiles are obtained.

The obtaining of the bio-information profiles may include obtaining the bio-information profiles by measuring bio-information of the user by using the bio-sensor during a predetermined period of time after the food intake.

The predetermined number may be set based on an accuracy of the bio-sensor.

The predetermined number may be set to a greater value as the accuracy of the bio-sensor decreases.

The bio-information may be a concentration of an in vivo analyte, and the analyte may include at least one of glucose, triglyceride, urea, uric acid, lactate, protein, cholesterol, antioxidant, and ethanol.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
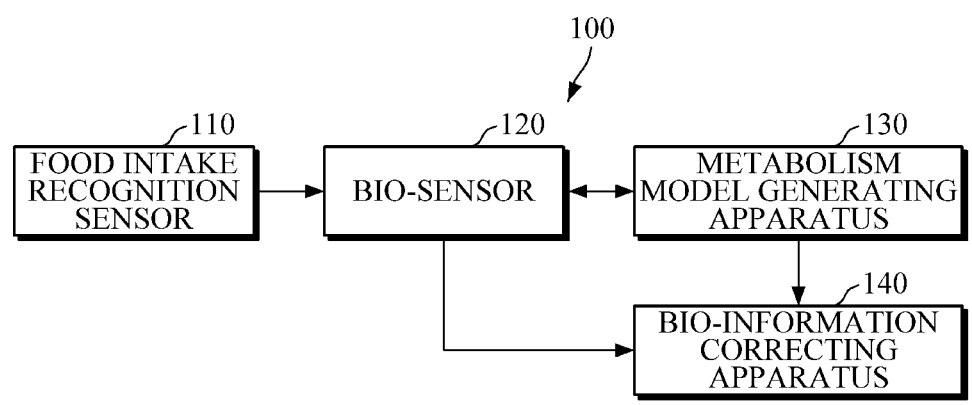
FIG. 1 is a block diagram illustrating an example of a bio-information estimating apparatus according to an embodiment.

Throughout the drawings and the detailed description, unless otherwise described, the same reference numerals may refer to the same elements, features, and structures. The relative size and depiction of the elements, features, and structures may be exaggerated for clarity, illustration, and convenience.

DETAILED DESCRIPTION

Hereinafter, embodiments of the present disclosure will be described in detail with reference to the accompanying drawings. It should be noted that wherever possible, the same reference numerals refer to the same parts even in different drawings. In the following description, a detailed description of known functions and configurations incorporated herein may be omitted so as to not obscure the subject matter of the present disclosure.

Process steps described herein may be performed differently from a specified order, unless a specified order is clearly stated in the context of the disclosure. That is, each step may be performed in a specified order, at substantially the same time, or in a reverse order.

It should be understood that, although terms such as "first," "second," etc., may be used herein to describe various elements, these elements should not be limited by these terms. These terms may be used to distinguish one element from another. Any references to the singular forms of terms may include the plural forms of the terms unless expressly stated otherwise, in the present disclosure, it should be understood that terms such as "including," "having," etc., may indicate the existence of the features, numbers, steps, actions, components, parts, or combinations thereof, disclosed in the specification, and might not preclude the possibility that one or more other features, numbers, steps, actions, components, parts, or combinations thereof, may exist or may be added.

Further, components described in the specification may be discriminated according to functions mainly performed by the components. That is, two or more components may be integrated into a single component. Furthermore, a single component may be separated into two or more components. Moreover, each component may additionally perform some or all of a function executed by another component in addition to the main function thereof. Some or all of the main function of each component may be carried out by another component. Each component may be implemented in hardware or software, or a combination thereof.

FIG. 1 is a block diagram illustrating an example of a bio-information estimating apparatus according to an embodiment. The bio-information estimating apparatus 100 is an apparatus for estimating bio-information of users by considering each user's metabolic reactions, and may be embedded in an electronic device or may be enclosed in a housing to be provided as a separate device. In this case, examples of the electronic device may include a cellular phone, a smartphone, a tablet personal computer (PC), a laptop computer, a personal digital assistant (PDA), a portable multimedia player (PMP), a navigation device, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

The bio-information may be the concentration of an in vivo analyte, and examples of the analyte may include, but are not limited to, glucose, triglyceride, urea, uric acid, lactate, protein, cholesterol, antioxidant (e.g., vitamin, carotenoid, flavonoid, ascorbic acid, tocopherol, etc.) ethanol, and the like. In addition, in the case where an in vivo analyte is glucose, the bio-information may indicate blood glucose. Hereinafter, description will be given of an embodiment in which bio-information is blood glucose for convenience of explanation.

Referring to FIG. 1, the bio-information estimating apparatus 100 includes a food intake recognition sensor 110, a bio-sensor 120, a metabolism model generating apparatus 130, and a bio-information correcting apparatus 140. The food intake recognition sensor 110, the bio-sensor 120, the metabolism model generating apparatus 130, and the bio-information correcting apparatus 140 may be implemented as separate hardware devices, or may be implemented in a single hardware device.

The food intake recognition sensor 110 may recognize a user's food intake, and may generate food intake sensor information. The food intake recognition sensor 110 may be implemented as a separate hardware device to be attached or worn on a user's body part, or may be embedded in the bio-sensor 120, the metabolism model generating apparatus 130 and/or the bio-information correcting apparatus 140.

In an embodiment, the food intake recognition sensor 110 may include a sensor for recognizing food intake from movements of the mouth, larynx, esophagus, and the like. Alternatively, the food intake recognition sensor 110 may include a sensor for recognizing food intake from physiological changes. For example, the food intake recognition sensor 110 may include, but is not limited to, various sensors implemented using a method of detecting food intake sounds, a method of capturing images of food and analyzing the food images, a method of detecting arm movements, a method of detecting swallowing or muscle movements of the neck, a method of detecting chest movements or breathing, a method of measuring a change in body temperature, a method of measuring a change in blood flow, a method of measuring a change in bio-information, and the like. That is, there is no limitation on the size or type of the food intake recognition sensor 110 as long as the food intake recognition sensor 110 may recognize a user's food intake.

Based on the type of the food intake recognition sensor 110, the food intake sensor information may include the food intake sounds, the captured food images, the detected arm movement information, swallowing information, neck muscle movement information, chest movement information, breathing information, body temperature change information, blood flow change information, and the like.

The bio-sensor 120 may measure a user's blood glucose levels. Further, in response to recognition of a user's food intake, the bio-sensor 120 may be controlled by the metabolism model generating apparatus 130 to measure a user's blood glucose levels at predetermined time intervals during a predetermined period of time, so as to obtain bio-information profiles. The bio-sensor 120 may be attached or worn on an object portion of the user to measure the user's blood glucose levels. For example, the bio-sensor 120 may be a non-invasive sensor which measures blood glucose levels based on various types of information such as measurement information, spectrum information measured by a spectrometer, impedance measurement information, ultrasound measurement information, heat measurement information, electrocardiogram (ECG) information, electroencephalogram (EEG) information, electromyogram (EMG) information, electrooculogram (EOG) information, photoplethysmogram (PPG) information, and the like. However, the bio-sensor 120 is not limited thereto, and may be an invasive sensor or a minimally invasive sensor. That is, there is no limitation on the size or type of the bio-sensor 120 as long as the bio-sensor 120 may measure a user's blood glucose levels.

The metabolism model generating apparatus 130 may control the bio-sensor 120 to cause the bio-sensor 120 to obtain a predetermined number of bio-information profiles. In this case, the predetermined number may be preset based on the accuracy of the bio-sensor 120. For example, as the accuracy of the bio-sensor 120 decreases, the predetermined number may be set to a greater value. Further, based on the predetermined number of bio-information profiles being obtained, the metabolism model generating apparatus 130 may generate a metabolism model for correcting errors of the bio-sensor 120 by using the obtained predetermined number of bio-information profiles. In this case, the metabolism model may be a bio-information model which reflects each individual's physiological characteristics.

The metabolism model generating apparatus 130 will be described in detail later with reference to FIGS. 2 and 3.

The bio-information correcting apparatus 140 may receive food intake sensor information from the food intake recognition sensor 110, and may receive blood glucose information from the bio-sensor 120.

The bio-information correcting apparatus 140 may obtain the food intake information by analyzing the received food intake sensor information and/or a change in blood glucose levels; or may obtain food intake information which is directly input by a user. The food intake information may include types of food consumed by a user, an amount of food intake, a time of food intake, and the like.

The bio-information correcting apparatus 140 may correct a blood glucose value measured by the bio-sensor 120 using the food intake information and the metabolism model. In an embodiment, based on obtaining the food intake information, the bio-information correcting apparatus 140 may estimate a blood glucose value by applying the obtained food intake information to the metabolism model, and may correct the blood glucose value, measured by the bio-sensor 120, based on the blood glucose value estimated using the metabolism model.

For example, the bio-information correcting apparatus 140 may generate bio-information guidelines by using the blood glucose value estimated using the metabolism model; and if the blood glucose value measured by the bio-sensor 120 deviates from the guideline, the bio-information correcting apparatus 140 may correct the blood glucose value, measured by the bio-sensor 120, to a blood glucose value within the bio-information guideline. In this case, the bio-information guidelines may indicate an allowable range of a user's blood glucose values determined based on the metabolism model.

In another example, the bio-information correcting apparatus 140 may correct the blood glucose value, measured by the bio-sensor 120, by weighted summation of a blood glucose value estimated using the metabolism model and a blood glucose value measured by the bio-sensor 120.

Figure 2:
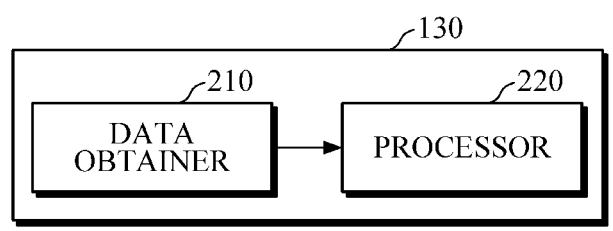
FIG. 2 is a block diagram illustrating an example of a metabolism model generating apparatus according to an embodiment.

FIG. 2 is a block diagram illustrating an example of a metabolism model generating apparatus according to an embodiment.

Referring to FIG. 2, the metabolism model generating apparatus 130 includes a data obtainer 210 and a processor 220.

The data obtainer 210 may obtain a predetermined number of bio-information profiles from the bio-sensor 120. In this case, the bio-information profiles may be a set of a user's blood glucose data measured by the bio-sensor 120 at predetermined time intervals during a predetermined period of time after food intake.

In an embodiment, the data obtainer 210 may obtain the bio-information profiles from the bio-sensor 120 by using wired or wireless communication techniques. In this case, examples of the wireless communication techniques may include Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio-Frequency Identification (RFID) communication, third generation (3G) communication, fourth generation (4G) communication, fifth generation (5G) communication, and the like. However, this is merely exemplary and is not intended to be limiting.

The processor 220 may control the bio-sensor 120 to obtain the predetermined number of bio-information profiles. That is, in response to recognition of a user's food intake, the processor 220 may control the bio-sensor 120 to measure the user's blood glucose levels at predetermined time intervals during a predetermined period of time, so as to obtain the predetermined number of bio-information profiles.

Based on obtaining the predetermined number of bio-information profiles, the processor 220 may extract a representative bio-information profile from the predetermined number of bio-information profiles. In this case, the processor 220 may extract the representative bio-information profile by various representative value extraction algorithms using a mean value, a median value, filtering, machine learning (e.g., principal component analysis (PCA), etc.), and the like, but the representative bio-information profile is not limited thereto.

Based on extracting the representative bio-information profile, the processor 220 may generate a metabolism model by using the extracted representative bio-information profile.

In an embodiment, the metabolism model may be represented by the following Equations 1 to 3.

$$\frac{dG}{dt} = \begin{cases} \frac{Ra_{GutG}}{V} + \frac{Hepbal_G}{V} - k_1 G^{1.3} - k_2 I \\ \quad + \gamma \frac{dI}{dt}, \quad G \leq 10 \text{ mmol/L} \\ \frac{Ra_{GutG}}{V} + \frac{Hepbal_G}{V} - k_1 G^{1.3} - k_2 I \\ \quad + \gamma \frac{dI}{dt} - \frac{k_3 G - k_4}{V}, \quad G > 10 \text{ mmol/L} \end{cases}$$ [Equation 1]

Referring to Equation 1, G denotes the glucose concentration; $Ra_{GutG}$ denotes a glucose uptake into a mesenteric circulation; V denotes a parameter related to a user's weight (e.g., 20% of a user's weight); $Hepbal_G$ denotes hepatic glucose balance which reflects a sum of glucogenesis in the liver and the glucose uptake by the mesenteric circulation; I denotes an insulin concentration; γ denotes a control parameter of insulin with respect to glucose; $k_1$ denotes a parameter representing a non-insulin-mediated glucose uptake; $k_2$ denotes a parameter representing an insulin-mediated glucose uptake; and $k_3$ and $k_4$ respectively denote a slope and an intercept of renal glucose clearance.

The insulin concentration I may be represented by the following Equation 2 by reflecting the effect of a hormone (e.g., incretin or glucagon) on insulin secretion, in which the hormone is related to glucose regulation and insulin secretion (hereinafter referred to as a hormone).

$$\frac{dI}{dt} = k_7 G^{1.3} + k_8 h - k_9 I + \beta$$ [Equation 2]

Referring to Equation 2, $k_7$ and $k_8$ denote rates of insulin appearance for glucose and hormone respectively; $k_9$ denotes an insulin clearance rate; β denotes the effect of an addition regulator, i.e., the effect of other factors except glucose and hormone; and h denotes a hormone concentration.

The hormone concentration h may be represented by the following Equation 3 based on the concentration of glucose-dependent insulinotropic polypeptide (GIP).

$$\frac{dh}{dt} = \frac{Ra_h}{V} + k_5 Duod_G - k_6 h$$ [Equation 3]

Referring to Equation 3, $Ra_h$ denotes an appearance rate of incretin; denotes a glucose transport rate into the duodenum; $k_5$ denotes an appearance rate of incretin in the duodenum; and $k_6$ denotes a hormone clearance rate.

By optimizing the parameters of the above Equations 1 to 3 based on the extracted representative bio-information profile, the processor 220 may generate a metabolism model which reflects each user's physiological characteristics.

The above Equations 1 to 3 are merely examples of the metabolism model, and the metabolism model is not limited thereto. That is, the metabolism model may be represented in various manners, and may include all these metabolism models.

The processor 220 may generate guide information to induce a user to obtain a predetermined number of bio-information profiles for use in generating a metabolism model, and may provide the generated guide information for the user. For example, in the case where the predetermined number is set to 5, the processor 220 may generate guide information to induce a user's food intake (e.g., 75 g of sugar) every morning for five days, and may provide the guide information for the user. In this manner, the bio-sensor 120 may obtain five bio-information profiles in total by obtaining one profile per day, and the data obtainer 210 may obtain five bio-information profiles from the bio-sensor 120.

Figure 3:
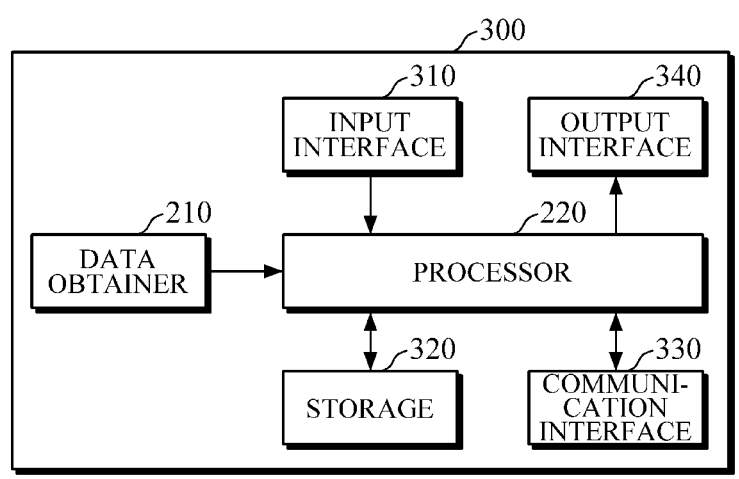
FIG. 3 is a block diagram illustrating another example of a metabolism model generating apparatus according to an embodiment.

FIG. 3 is a block diagram illustrating another example of a metabolism model generating apparatus according to an embodiment. The metabolism model generating apparatus 300 of FIG. 3 may be another example of the metabolism model generating apparatus 130 of FIG. 1.

Referring to FIG. 3, the metabolism model generating apparatus 300 includes the data obtainer 210, the processor 220, an input interface 310, a storage 320, a communication interface 330, and an output interface 340. Here, the data obtainer 210 and the processor 220 may be substantially similar to the data obtainer 210 and the processor 220 as described above with reference to FIG. 2, such that detailed description thereof may be omitted.

The input interface 310 may receive input of various operation signals from a user based on a user input. In an embodiment, the input interface 310 may include a keypad, a dome switch, a touch pad (e.g., static pressure sensitive touch pad, a capacitive touch pad, etc.), a jog wheel, a jog switch, a hardware (H/W) button, and the like. Particularly, the touch pad, which forms a layer structure with a display, may be called a touch screen.

The storage 320 may store programs or instructions for operation of the metabolism model generating apparatus 300, data input to the metabolism model generating apparatus 300, data obtained by the metabolism model generating apparatus 300, and data processed by the metabolism model generating apparatus 300. In addition, the storage 320 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the metabolism model generating apparatus 300 may communicate with an external storage medium, such as web storage and the like, which performs a storage function of the storage 320 via the Internet.

The communication interface 330 may perform communication with an external device. For example, the communication interface 330 may transmit, to the external device, the data input to and stored in the metabolism model generating apparatus 300, the data obtained and processed by the metabolism model generating apparatus 300, and the like, or may receive, from the external device, various data for estimating bio-information.

In this case, the external device may be medical equipment using the data input to and stored in the metabolism model generating apparatus 300, the data obtained and processed by the metabolism model generating apparatus 300, and the like, a printer to print out results, or a display to display the results. In addition, the external device may be a digital television (TV), a desktop computer, a cellular phone, a smartphone, a tablet PC, a laptop computer, a personal digital assistant (PDA), a portable multimedia player (PMP), a navigation device, an MP3 player, a digital camera, a wearable device, and the like, but is not limited thereto.

The communication interface 330 may communicate with an external device by using wired or wireless communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, Wi-Fi communication, Radio-Frequency Identification (RFID) communication, 3G communication, 4G communication, 5G communication, and the like. However, this is merely exemplary and is not intended to be limiting.

The output interface 340 may output the data input to and stored in the metabolism model generating apparatus 300, the data obtained and processed by the metabolism model generating apparatus 300, and the like. In an embodiment, the output interface 340 may output the data input to and stored in the metabolism model generating apparatus 300, the data obtained and processed by the metabolism model generating apparatus 300, and the like, by using at least one of an acoustic method, a visual method, and a tactile method. To this end, the output interface 340 may include a display, a speaker, a vibrator, and the like.

Figure 4:
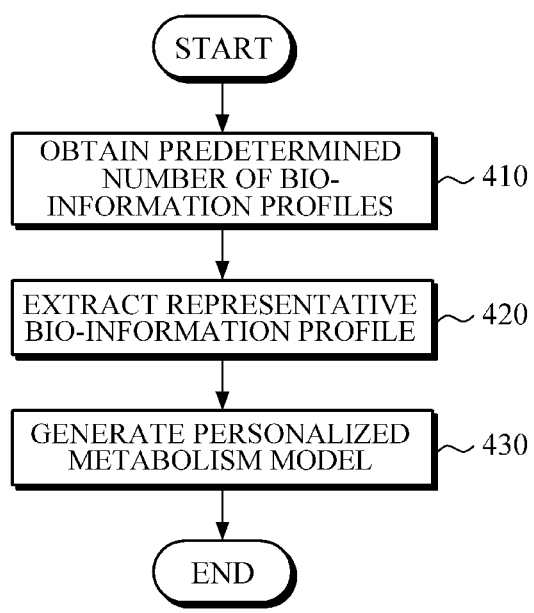
FIG. 4 is a flowchart illustrating an example of a metabolism model generating method according to an embodiment.

FIG. 4 is a flowchart illustrating an example of a metabolism model generating method according to an embodiment. The metabolism model generating method may be performed by the metabolism model generating apparatuses 130 and 300 of FIGS. 2 and 3.

Referring to FIG. 4, the metabolism model generating apparatus may obtain a predetermined number of bio-information profiles from a bio-sensor in operation 410. For example, the metabolism model generating apparatus may obtain the bio-information profiles from the bio-sensor by using wired or wireless communication techniques. In this case, the predetermined number may be preset based on the accuracy of the bio-sensor, and the bio-information profiles may be a set of a user's blood glucose data measured by the bio-sensor at predetermined time intervals during a predetermined period of time after food intake.

Based on obtaining the predetermined number of bio-information profiles, the metabolism model generating apparatus may extract a representative bio-information profile from the predetermined number of bio-information profiles in operation 420. In this case, the metabolism model generating apparatus may extract the representative bio-information profile by various representative value extraction algorithms using a mean value, a median value, filtering, machine learning (e.g., principal component analysis (PCA), etc.), and the like, but the representative bio-information profile is not limited thereto.

Based on extracting the representative bio-information profile, the metabolism model generating apparatus may generate a personalized metabolism model by using the extracted representative bio-information profile in operation 430. For example, the metabolism model generating apparatus may generate the metabolism model by optimizing the parameters of the Equations 1 to 3 shown above using the representative bio-information profile. However, Equations 1 to 3 are merely examples of the metabolism model, and the metabolism model is not limited thereto.

Furthermore, the metabolism model generating apparatus may generate guide information for inducing a user to obtain the predetermined number of bio-information profiles, and may provide the guide information for the user.

Figure 5:
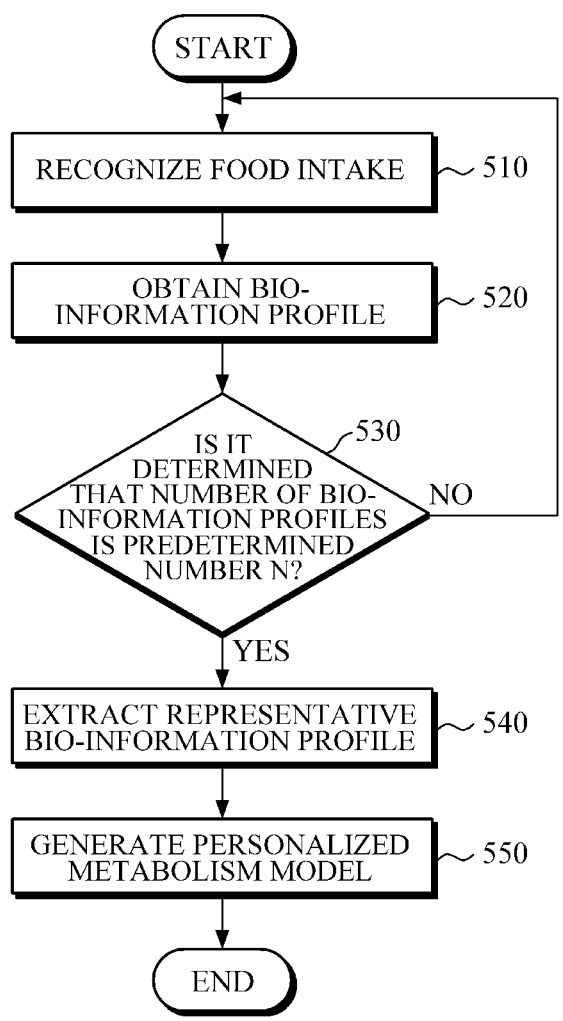
FIG. 5 is a flowchart illustrating another example of a metabolism model generating method according to an embodiment.

FIG. 5 is a flowchart illustrating another example of a metabolism model generating method according to an embodiment. The metabolism model generating method of FIG. 5 may be performed by the bio-information estimating apparatus 100.

Referring to FIG. 5, the bio-information estimating apparatus may recognize a user's food intake in operation 510. For example, the bio-information estimating apparatus may recognize the user's food intake by using various methods, such as a method of detecting food intake sounds, a method of capturing images of food and analyzing the food images, a method of detecting arm movements, a method of detecting swallowing or muscle movements of the neck, a method of detecting chest movements or breathing, a method of measuring a change in body temperature, a method of measuring a change in blood flow, a method of measuring a change in bio-information, and the like.

Based on recognizing the user's food intake, the bio-information estimating apparatus may measure a user's blood glucose levels at predetermined intervals during a predetermined period of time by using a bio-sensor, so as to obtain bio-information profiles in operation 520.

The bio-information estimating apparatus may determine whether a number of the obtained bio-information profiles is a predetermined number n in operation 530; and if the number of the obtained bio-information profiles is not the predetermined number n (operation 530—NO), then the bio-information estimating apparatus may return to operation 510 to repeat the operations 510 to 530 until the predetermined number n of the bio-information profiles are obtained.

If the number of the bio-information profiles reaches the predetermined number n (operation 530—YES), then the bio-information estimating apparatus may extract a representative bio-information profile from the predetermined number n of the bio-information profiles in operation 540. In this case, the bio-information estimating apparatus may extract the representative bio-information profile by various representative value extraction algorithms using a mean value, a median value, filtering, machine learning (e.g., principal component analysis (PCA), etc.), and the like, but the representative bio-information profile is not limited thereto.

Based on extracting the representative bio-information profile, the bio-information estimating apparatus may generate a personalized metabolism model by using the extracted representative bio-information profile in operation 550. For example, the bio-information estimating apparatus may generate the metabolism model by optimizing the parameters of Equations 1 to 3 shown above using the representative bio-information profile. However, Equations 1 to 3 are merely examples of the metabolism model, and the metabolism model is not limited thereto.

Figure 6:
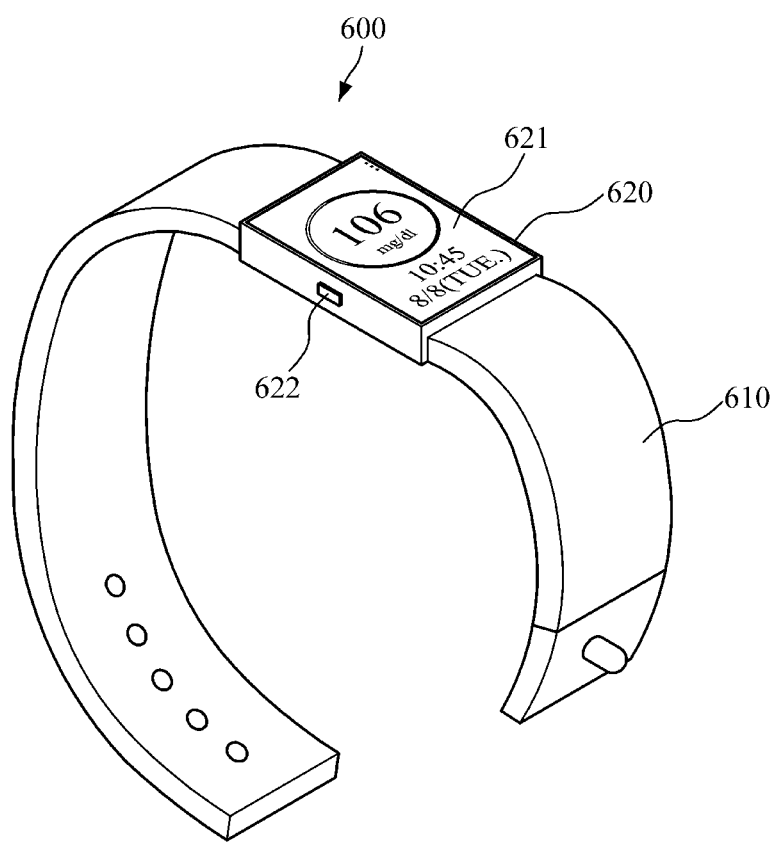
FIG. 6 is a diagram illustrating an example of a wrist-type wearable device according to an embodiment.

FIG. 6 is a diagram illustrating an example of a wrist-type wearable device according to an embodiment.

Referring to FIG. 6, the wrist-type wearable device 600 includes a strap 610 and a main body 620.

The strap 610 may be connected to both ends of the main body 620 so as to be fastened in a detachable manner or may be integrally formed therewith as a smart band. The strap 610 may be made of a flexible material to be wrapped around a user's wrist so that the main body 620 may be worn on the wrist.

The main body 620 may include the food intake recognition sensor 110, the bio-sensor 120, the metabolism model generating apparatuses 130 and 300, and/or the bio-information correcting apparatus 140 described above. Further, the main body 620 may include a battery which supplies power to the wrist-type wearable device 600, the food intake recognition sensor 110, the bio-sensor 120, the metabolism model generating apparatuses 130 and 300, and the bio-information correcting apparatus 140.

The bio-sensor may be mounted at the bottom of the main body 620 to be exposed to a user's wrist. Accordingly, when a user wears the wrist-type wearable device 600, the bio-sensor may contact the user's skin.

The wrist-type wearable device 600 may further include a display 621 and an input interface 622 which are provided on the main body 620. The display 621 may display data processed by the wrist-type wearable device 600, the food intake recognition sensor 110, the bio-sensor 120, the metabolism model generating apparatuses 130 and 300, and the bio-information correcting apparatus 140, processing result data thereof, and the like. The input interface 622 may receive various operation signals from a user based on a user input.

The embodiments of the present disclosure may be realized as computer-readable code stored on a non-transitory computer-readable medium. The computer-readable medium may be any type of recording device in which data is stored in a computer-readable manner. Examples of the computer-readable medium may include a ROM, a RAM, a CD-ROM, a magnetic tape, a floppy disc, an optical data storage, and a carrier wave (e.g., data transmission through the Internet). The computer-readable medium may be distributed via a plurality of computer systems connected to a network so that computer-readable code is written thereto and executed therefrom in a decentralized manner.

The present disclosure has been described herein with regard to the various embodiments. However, it should be apparent to those skilled in the art that various changes and modifications may be made without departing from the scope of the present disclosure. Thus, it is clear that the above-described embodiments are illustrative in all aspects and are not intended to limit the present disclosure.

What is claimed is:

1. An apparatus for generating a metabolism model, the apparatus comprising:
   a processor configured to:
   obtain, from a bio-sensor, a predetermined number of bio-information profiles that is set based on an accuracy of the bio-sensor;
   extract a representative bio-information profile from the obtained predetermined number of bio-information profiles; and
   generate the metabolism model for correcting an error of the bio-sensor by using the extracted representative bio-information profile.

2. The apparatus of claim 1, wherein the bio-information profiles correspond to a user's bio-information data measured by the bio-sensor during a predetermined period of time after food intake.

3. The apparatus of claim 1, wherein the predetermined number is set to a greater value as the accuracy of the bio-sensor decreases.

4. The apparatus of claim 1, wherein the metabolism model is configured to obtain information of a concentration of an in vivo analyte, and
   wherein the analyte comprises at least one of glucose, triglyceride, urea, uric acid, lactate, protein, cholesterol, antioxidant, and ethanol.

5. The apparatus of claim 1, wherein the processor is configured to extract the representative bio-information profile from the obtained predetermined number of bio-information profiles by using at least one of a mean value, a median value, filtering, and machine learning.

6. The apparatus of claim 1, wherein the processor is further configured to:
   generate guide information for inducing a user to obtain the predetermined number of bio-information profiles; and
   provide the guide information to the user.

7. A method of generating a metabolism model, the method comprising:
   obtaining, from a bio-sensor, a predetermined number of bio-information profiles that is set based on an accuracy of the bio-sensor;
   extracting a representative bio-information profile from the obtained predetermined number of bio-information profiles; and
   generating the metabolism model for correcting an error of the bio-sensor by using the extracted representative bio-information profile.

8. The method of claim 7, wherein the bio-information profiles correspond to a user's bio-information data measured by the bio-sensor during a predetermined period of time after food intake.

9. The method of claim 7, wherein the predetermined number is set to a greater value as the accuracy of the bio-sensor decreases.

10. The method of claim 7, further comprising:
    obtaining information of a concentration of an in vivo analyte using the metabolism model, and
    wherein the analyte comprises at least one of glucose, triglyceride, urea, uric acid, lactate, protein, cholesterol, antioxidant, and ethanol.

11. The method of claim 7, wherein the extracting of the representative bio-information profile comprises extracting the representative bio-information profile from the obtained predetermined number of bio-information profiles by using at least one of a mean value, a median value, filtering, and machine learning.

12. The method of claim 7, further comprising:
    generating guide information for inducing a user to obtain the predetermined number of bio-information profiles; and
    providing the guide information to the user.

13. A method of generating a metabolism model, the method comprising:
    recognizing a user's food intake;
    based on recognizing the user's food intake, obtaining a predetermined number of bio-information profiles by using a bio-sensor;
    based on obtaining the predetermined number of bio-information profiles, extracting a representative bio-information profile from the obtained predetermined number of bio-information profiles; and
    generating the metabolism model for correcting an error of the bio-sensor by using the extracted representative bio-information profile.

14. The method of claim 13, further comprising:
    repeating the recognizing of the food intake and the obtaining of the bio-information profiles until the predetermined number of bio-information profiles are obtained.

15. The method of claim 13, wherein the obtaining of the bio-information profiles comprises obtaining the bio-information profiles by measuring bio-information of the user by using the bio-sensor during a predetermined period of time after the food intake.

16. The method of claim 13, wherein the predetermined number is set based on an accuracy of the bio-sensor.

17. The method of claim 16, wherein the predetermined number is set to a greater value as the accuracy of the bio-sensor decreases.

18. The method of claim 13, further comprising:
obtaining information of a concentration of an in vivo analyte using the metabolism model, and
wherein the analyte comprises at least one of glucose, triglyceride, urea, uric acid, lactate, protein, cholesterol, antioxidant, and ethanol.

* * * * *